United States Patent [19]

Innes et al.

[11] Patent Number: 5,081,323

[45] Date of Patent: * Jan. 14, 1992

[54] LIQUID PHASE ALKYLATION OR TRANSALKYLATION PROCESS USING ZEOLITE BETA

[75] Inventors: Robert A. Innes, San Rafael; Stacey I. Zones, San Francisco; Gerald J. Nacamuli, Mill Valley, all of Calif.

[73] Assignee: Chevron Research and Technology Company, San Francisco, Calif.

[*] Notice: The portion of the term of this patent subsequent to Jan. 2, 2007 has been disclaimed.

[21] Appl. No.: 441,137

[22] Filed: Nov. 22, 1989

Related U.S. Application Data

[63] Continuation of Ser. No. 134,410, Dec. 17, 1987, Pat. No. 4,891,458.

[51] Int. Cl.$^5$ ............................................. C07C 2/66

[52] U.S. Cl. ................................... 585/449; 585/453; 585/467

[58] Field of Search ......................... 585/467, 449, 453

[56] References Cited

U.S. PATENT DOCUMENTS

| | | | |
|---|---|---|---|
| 2,431,166 | 11/1947 | Buell et al. | 585/449 |
| 3,478,119 | 11/1969 | Maier et al. | 585/449 |
| 3,751,504 | 8/1973 | Keown et al. | 585/449 |

*Primary Examiner*—Anthony McFarlane
*Attorney, Agent, or Firm*—Richard J. Sheridan; Thomas G. DeJonghe

[57] ABSTRACT

A process for the alkylation or transalkylation of an aromatic hydrocarbon which comprises contacting the aromatic hydrocarbon with a $C_2$ to $C_4$ olefin alkylating agent or a polyalkyl aromatic hydrocarbon transalkylating agent, under at least partial liquid phase conditions, and in the presence of a catalyst comprising zeolite beta.

16 Claims, No Drawings

LIQUID PHASE ALKYLATION OR TRANSALKYLATION PROCESS USING ZEOLITE BETA

This is a continuation of application Ser. No. 134,410, filed Dec. 17, 1987, now U.S. Pat. No. 4,891,458.

BACKGROUND OF THE INVENTION

The present invention relates to a process for preparing mono-alkylated aromatic compounds by subjecting an aromatic hydrocarbon to alkylation with a $C_2$ to $C_4$ olefin or transalkylation with a polyalkyl aromatic hydrocarbon, under at least partial liquid phase conditions, utilizing zeolite beta as the alkylation/transalkylation catalyst.

Most industrial processes for the alkylation and/or transalkylation of aromatic hydrocarbons employ a Friedel-Crafts type of catalyst such as aluminum chloride, boron trifluoride, hydrofluoric acid, liquid and solid phosphoric acid, sulfuric acid and the like. These materials are highly corrosive to process equipment, cause many operational problems, and are often difficult to dispose of in an environmentally acceptable manner.

It has long been a goal of research to find noncorrosive, solid catalysts to replace the Friedel-Crafts catalysts. To this end, various types of zeolite catalysts have been proposed.

U.S. Pat. No. 2,904,607 shows the alkylation of aromatic hydrocarbons in the presence of a crystalline metallic aluminosilicate having a uniform pore opening of 6 to 15Å units. Sodium and magnesium aluminosilicates are cited as examples.

U.S. Pat. No. 3,251,897 describes a process wherein the alkylation reaction is carried out at a temperature not more than 600° F., preferably under substantially liquid phase conditions. The catalysts for this process are crystalline aluminosilicates (i.e., zeolites), which contain hydrogen and/or a rare earth element and which have a uniform pore size of at least 6Å. The rare earth and hydrogen forms of zeolite types X, Y, and mordenite are specifically disclosed.

U.S. Pat. No. 3,385,906 describes a process for transalkylating benzene and diisopropylbenzene to make cumene in the presence of a zeolite molecular sieve catalyst wherein not more than 90% of aluminum atoms in the zeolite are associated with monovalent cations.

U.S. Pat. No. 3,631,120 describes an alkylation process wherein the zeolite catalyst has a silica-to-alumina ratio from about 4.0 to about 4.9 and is activated by ammonium exchange followed by calcuation U.S. Pat. No. 3,641,177 describes an alkylation process wherein the zeolite component of the catalyst has undergone a series of ammonium exchange, calcination, and steam treatments. The catalyst employed in the examples would be described now as an "ultrastable" or "steam stabilized" Y zeolite.

U.S. Pats. Nos. 3,769,360, 3,776,971, 3,778,415, 3,843,739, and 4,459,426 relate to methods for combining alkylation and transalkylation to obtain improved yields of monoalkylated aromatics. Rare earth exchanged Y (RE-Y) and steam stabilized Y zeolites are cited in these patents as being particularly effective catalysts.

European Pat. Application No. 7,126 shows the advantages of zeolite omega for alkylating benzene with propylene to make cumene. Compared to zeolites RE-Y, L, and steam stabilized Y, only zeolite omega was able to meet cumene purity specifications while achieving a run length of 500 hours.

European Patent Application No. 30,084 shows the alkylation of benzene with dodecene over zeolites ZSM-4, beta, ZSM-20, Linde Type L, ZSM-38 and RE-Y.

U.S. Pat. Nos. 3,751,504 and 3,751,506 show transalkylation and alkylation in the vapor phase over ZSM-5 type zeolite catalysts. ZSM-5 is a medium pore size zeolite having an effective pore size between 5 and 6Å.

U.S. Pat. No. 4,049,737 relates to the selective propylation of toluene to make cymene over ZSM-5.

Alkylation or transalkylation over other medium pore size ZSM-type zeolites is taught in U.S. Pat. Nos. 4,016,245 (ZSM-35), 4,046,859 (ZSM-21), 4,070,407 (ZSM-35 and ZSM-38) 4,076,842 (ZSM-23), 4,291,185 (ZSM-12), 4,387,259 (ZSM-12), 4,547,605 (ZSM-23).

Despite the available literature on zeolite catalysis and the recognized advantages of replacing the Friedel-Crafts catalysts with a noncorrosive catalyst, zeolites have not yet found widespread use in industrial alkylation processes. Under commercially realistic conditions, the zeolite catalysts described in the literature have tended to deactivate rapidly due to fouling, produced the desired product in a lower yield than the competing Friedel-Crafts catalyst, or made a product which failed to meet established purity specifications. The one notable exception is the use of a ZSM-5 type catalyst for the vapor phase alkylation of benzene with ethylene to make ethylbenzene.

SUMMARY OF THE INVENTION

The present invention provides a process for the alkylation or transalkylation of an aromatic hydrocarbon which comprises contacting the aromatic hydrocarbon with a $C_2$ to $C_4$ olefin alkylating agent or a polyalkyl aromatic hydrocarbon transalkylating agent, under at least partial liquid phase conditions, and in the presence of a catalyst comprising zeolite beta.

Among other factors, the present invention is based on the discovery that aromatic hydrocarbons, such as benzene, toluene or xylene, can be effectively alkylated with lower ($C_2$–$C_4$) olefins or transalkylated with polyalkyl aromatic hydrocarbons, using a zeolite beta catalyst which provides monoalkylated products in high yield and high product purity. Surprisingly, the zeolite beta catalyst is able to provide high yields of monoalkylated product for much longer periods of time than other zeolite catalysts.

In a further embodiment of the present invention, monoalkylated aromatic hydrocarbons are prepared in high yield by combining alkylation and transalkylation in a process which comprises:

(a) contacting a stoichiometric excess of an aromatic hydrocarbon feed with a $C_2$ to $C_4$ olefin in an alkylation zone under at least partial liquid phase conditions and in the presence of a catalyst comprising zeolite beta;

(b) separating the product from step (a) into fractions comprising (1) an aromatic hydrocarbon fraction, (2) a monoalkyl aromatic hydrocarbon fraction and (3) a polyalkyl aromatic hydrocarbon fraction; and (c) contacting the polyalkyl aromatic hydrocarbon fraction with additional aromatic hydrocarbon feed in a transalkylation zone under at least partial liquid phase conditions and in the presence of a catalyst comprising zeolite beta.

DETAILED DESCRIPTION OF THE INVENTION

Zeolite beta is a known synthetic crystalline aluminosilicate originally described in U.S. Pat. Nos. 3,308,069 and Re 28,341, to which reference is made for further details of this zeolite, its preparation and properties. Zeolite beta is identified by its characteristic X-ray diffraction pattern, which is set out in Table 4 of U.S. Pat. Nos. 3,308,069 and Re 28,341. This pattern, in terms of the significant d values (Angstroms, radiation:K alpha doublet of copper, Geiger counter spectrometer), is reproduced in Table 1 below.

TABLE 1

| d Values of Reflection in Zeolite Beta |
|---|
| 11.4 ± 0.2 |
| 7.4 ± 0.2 |
| 6.7 ± 0.2 |
| 4.25 ± 0.1 |
| 3.97 ± 0.1 |
| 3.0 ± 0.1 |
| 2.2 ± 0.1 |

U.S. Pat. Nos. 3,308,069 and Re 28,341 describe the composition of zeolite beta in its as-synthesized form as follows:

$$[XNa(1.0\pm0.1-X)TEA]AlO_2 \cdot Y\ SiO_2 \cdot W\ H_2O$$

wherein X is less than 1, preferably less than 0.75, TEA represents tetraethylammonium ion, Y is greater than 5 and less than 100, and W is up to about 4, depending on the condition of dehydration and on the metal cation present. These patents also teach that the sodium may be replaced by another metal ion using ion exchange techniques.

Subsequent publications such as European Patent Applications Nos. 95,304, 159,846, 159,847, and 164,939 have broadened the definition of zeolite beta to include materials prepared using templating agents other than tetraethylammonium hydroxide and materials having Si/Al atomic ratios greater than 100. Also, the zeolites described in European Patent Applications Nos. 55,046 ("Nu-2") and 64,328 and British Patent Application No. 2,024,790 ("Boralite B") have structures and X-ray diffraction patterns very similar to that of zeolite beta and are included within the scope of the term "zeolite beta", as used herein.

The forms of zeolite beta which are most useful in the present invention are crystalline aluminosilicates having the empirical formula:

$$(X/n)\ M \cdot (1.0\pm0.1-X)\ Q \cdot AlO_2 \cdot Y\ SiO_2 \cdot W\ H_2O$$

wherein X is less than 1, preferably less than 0.75, Y is greater than 5 and less than 100, W is up to about 4, M is a metal ion, n is the valence of M, and Q is a hydrogen ion, an ammonium ion or an organic cation, or a mixture thereof. For purposes of the present invention, Y is preferably greater than 5 and less than about 50. Consequently, the silicon to aluminum atomic ratio in the above formula is greater than 5:1 and less than 100:1, and preferably greater than 5:1 and less than about 50:1.

It is also contemplated that other elements, such as gallium, boron and iron, can be variably substituted for aluminum in the above formula. Similarly, elements such as germanium and phosphorus can be variably substituted for silicon.

Suitable organic cations are those cations which are derived in aqueous solution from tetraethylammonium bromide or hydroxide, dibenzyl-1,4-diazabicyclo[2.2.2]octane chloride, dimethyldibenzyl ammonium chloride, 1,4-di(1-azonium bicyclo[2.2.2]octane)butane dibromide or dihydroxide, and the like. These organic cations are known in the art and are described, for example, in European Patent Applications Nos. 159,846 and 159,847, and U.S. Pat. No. 4,508,837. The preferred organic cation is the tetraethylammonium ion.

M is typically a sodium ion from the original synthesis but may also be a metal ion added by ion exchange techniques. Suitable metal ions include those from Groups IA, IIA or IIIA of the Periodic Table or a transition metal. Examples of such ions include ions of lithium, potassium, calcium, magnesium, barium, lanthanum, cerium, nickel, platinum, palladium, and the like.

For high catalytic activity, the zeolite beta should be predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, a major portion of the cation sites are occupied by hydrogen ions and/or rare earth ions. It is especially preferred that at least 80% of the cation sites are occupied by hydrogen ions and/or rare earth ions.

The pure zeolite may used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 wt.% zeolite beta. Usually the zeolite beta content will range from 10 to 90 wt.%, and more typically from 60 to 80 wt.%. The preferred inorganic binder is alumina. The mixture may be formed into tablets or extrudates having the desired shape by methods well known in the art. The extrudates or tablets will usually be cylindrical in shape. Other shapes with enhanced surface-to-volume ratios, such as fluted or polylobed cylinders, can be employed to enhance mass transfer rates and, thus, catalytic activity.

Examples of suitable aromatic hydrocarbon feedstocks which may be alkylated or transalkylated by the process of the invention include aromatic compounds such as benzene, toluene and xylene. The preferred aromatic hydrocarbon is benzene. Mixtures of aromatic hydrocarbons may also be employed.

Suitable olefins for the alkylation of the aromatic hydrocarbon are those containing 2 to 4 carbon atoms, such as ethylene, propylene, butene-1, trans-butene-2 and cis-butene-2, or mixtures thereof. Preferred olefins are ethylene and propylene. An especially preferred olefin is propylene. These olefins may be present in admixture with the corresponding $C_2$ to $C_4$ paraffins, but it is usually preferable to remove dienes, acetylenes, water, sulfur compounds or nitrogen compounds which may be present in the olefin feedstock stream, to prevent rapid catalyst deactivation. In some cases, however, it may be desirable to add, in a controlled fashion, small amounts of water or nitrogen compounds to optimize catalytic properties.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), diisopropylbenzene, triisopropylbenzene, diisopropyltoluene, dibutylbenzene, and the like. Preferred polyalkyl aromatic hydrocarbons are the dialkyl benzenes. A particularly preferred polyalkyl aromatic hydrocarbon is diisopropylbenzene.

Reaction products which may be obtained from the process of the invention include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and sec-butylbenzene from the reaction of benzene and n-butenes or polybutylbenzenes. The production of cumene from the alkylation of benzene with propylene or the transalkylation of benzene with di-isopropylbenzene is especially preferred.

When alkylation is the process conducted according to this invention, reaction conditions are as follows. The aromatic hydrocarbon feed should be present in stoichiometric excess. It is preferred that the molar ratio of aromatics to olefins be at least about four to one (4:1) to prevent rapid catalyst fouling. The reaction temperature may range from 100° F. to 600° F., preferably, 250° to 450° F. In the case of cumene production, a temperature range of 250° F. to 375° F. is most preferred to reduce product impurities. The reaction pressure should be sufficient to maintain at least a partial liquid phase in order to retard catalyst fouling. This is typically 50 to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted according to the invention, the molar ratio of aromatic hydrocarbon to polyalkyl aromatic hydrocarbon will generally range from about 1:1 to about 50:1, and preferably from about 2:1 to about 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hour space velocity will range from about 0.1 to 10.

When conducting either alkylation or transalkylation, various types of reactors can be used in the process of this invention. For example, the process can be carried out in batchwise fashion by adding the catalyst and aromatic feedstock to a stirred autoclave, heating to reaction temperature, and then slowly adding the olefinic or polyalkylaromatic feedstock. A heat transfer fluid can be circulated through the jacket of the autoclave, or a condenser can be provided to remove the heat of reaction and maintain a constant temperature. Large scale industrial processes may employ a fixed bed reactor operating in an upflow or downflow mode or a moving bed reactor operating with concurrent or countercurrent catalyst and hydrocarbon flows. These reactors may contain a single catalyst bed or multiple beds and may be equipped for the interstage addition of olefins and interstage cooling. Interstage olefin addition and more nearly isothermal operation enhance product quality and catalyst life. A moving bed reactor makes possible the continuous removal of spent catalyst for regeneration and replacement by fresh or regenerated catalysts.

In a preferred embodiment of the present invention, the alkylation process is carried out with addition of olefin in at least two stages. Preferably, there will be two or more catalyst beds or reactors in series, wherein at least a portion of the olefin is added between the catalyst beds or reactors. Interstage cooling can be accomplished by the use of a cooling coil or heat exchanger. Alternatively, interstage cooling can be effected by staged addition of the aromatic feedstock, that is, by addition of the aromatic feedstock in at least two stages. In this instance, at least a portion of the aromatic feedstock is added between the catalyst beds or reactors, in similar fashion to the staged addition of olefin described above. The staged addition of aromatic feedstock provides additional cooling to compensate for the heat of reaction.

In a fixed bed reactor or moving bed reactor, alkylation is completed in a relatively short reaction zone following the introduction of olefin. Ten to thirty percent of the reacting aromatic molecules may be alkylated more than once. Transalkylation is a slower reaction which occurs both in the alkylation zone and in the remainder of the catalyst bed. If transalkylation proceeds to equilibrium, better than 90 wt.% selectivity to monoalkylated product is generally achieved. Thus, transalkylation increases the yield of monoalkylated product by reacting the polyalkylated products with additional benzene.

The alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies. In most cases, the recovered monoalkylated product must be very pure. For example, current specifications call for 99.9% cumene purity with less than 500 ppm each of ethylenzene and butylbenzene. Since only a small fraction of by-product ethylbenzene and n-propylbenzene can be economically removed by distillation, it is important to have a feedstock containing very little ethylene and a catalyst which makes very little of these impurities.

Additional monoalkylated product may be produced by transalkylation. The polyalkylated products may be recycled to the alkylation reactor to undergo transalkylation or they may be reacted with additional aromatic feed in a separate reactor. Usually, it is preferred to blend the bottoms from the distillation of monoalkylated product with a stoichiometric excess of the aromatic feed, and react the mixture in a separate reactor over a suitable transalkylation catalyst. The transalkylation catalyst is preferably a catalyst comprising zeolite beta. The effluent from the transalkylation reactor is blended with alkylation reactor effluent and the combined stream distilled. A bleed may be taken from the polyalkylated product stream to remove unreactive heavies from the loop or the polyalkylated product stream may be distilled to remove heavies prior to transalkylation.

The following examples are provided to illustrate the invention in accordance with the principles of the invention but are not to be construed as limiting the invention in any way except as indicated by the appended claims.

Abbreviations used in the following examples include "DIPB" for diisopropylbenzene and "TIPB" for triisopropylbenzene.

EXAMPLES

Example 1

Preparation of Zeolite Beta

A 524.06-gram portion of Ludox AS-30 silica sol was added dropwise to 20.85 gms of sodium aluminate $Na_2Al_2O_4 \cdot 3H_2O$ and 652.22 gms of 20% tetraethylammonium hydroxide solution. The mixture was stirred for two days without heat, then charged to a one-gallon autoclave. After six days in the autoclave at 150° C. and without stirring, a large amount of crystalline material had formed. This material was filtered, washed, and ovendried overnight at 100° C. to yield 141 gms of crystalline powder. The oven-dried material was calcined for 10 hours at 1000° F. Both the air-dried and calcined materials were identified by X-ray diffraction as zeolite beta.

Two more batches of zeolite beta were prepared identically to the first batch except that the amounts of the starting materials used were multiplied by 0.61 and 1.22 to yield 89.7 and 195.5 gms of oven-dried zeolite, respectively. In both cases, X-ray diffraction patterns confirmed that the oven-dried and calcined products were zeolite beta.

The combined calcined material was analyzed by ICP spectroscopy. The Si/Al atomic ratio was 13/1 and the sodium content was 0.3 wt.%. The surface area of the calcined zeolite measured by the nitrogen adsorption was 640 $m^2/g$.

Example 2

Ammonium Exchange of Zeolite Beta

A 355-gram portion of the calcined zeolite beta from Example 1 was divided into three equal portions which were each ammonium exchanged four times. The exchanges were carried out by soaking the zeolite in approximately two liters of 0.7 N ammonium nitrate solution overnight at 212° F. After each of the first three exchanges, the supernatant liquid was decanted off and fresh ammonium nitrate solution added. After the final exchange, the product was filtered, washed with distilled water, and oven-dried.

Example 3

Formation of Extrudates

The ammonium-exchanged zeolite beta from Example 2 was calcined for five hours at 1000° F. to convert the zeolite to its hydrogen form. A 320-gram portion of the calcined zeolite was dry-mixed with 112.7 gms of Catapal alumina (71% Al2O3). Distilled water and dilute nitric acid were added to peptize the alumina and bring the mixture to a consistency suitable for extrusion. A hydraulic press was used to extrude the mixture through a 1/16-inch die. The extrudates were collected in a large evaporating dish, oven-dried, then calcined at 400°–1000° F.

Example 4

Comparison of Zeolite Beta with Prior Art Catalysts in Cumene Catalyst Screening Test Various forms of zeolite beta catalyst as prepared above were compared with other zeolite catalysts known in the prior art to be useful for cumene synthesis. The catalysts tested were:

(1) Non-exchanged calcined zeolite betz powder from Example 1.
(2) Once exchanged zeolite betz powder prepared by treating four grams of the calcined zeolite from Example 1 with an equal weight of ammonium nitrate in 200 ml of solution for two hours at 212° F. The ammonium-exchanged material was recovered by filtration, washed and oven-dried.
(3) Zeolite beta 1/16-inch extrudates from Example 3.
(4) Linde SK-500 rare earth Y (RE-Y) zeolite in 1/16-inch extrudate form.
(5) Linde LZ-Y82 steam stabilized Y zeolite in powder form.
(6) Linde LZ-Y82 steam stabilized Y zeolite in 1/16-inch extrudate form.
(7) Linde ELZ-6 omega zeolite in powdered form.
(8) ZSM-5 ($SiO_2/Al_2O_3 = 70$) 1/16-inch extrudates formed from 65% zeolite and 35% alumina binder.

The powdered zeolites were pressed to form tablets which were crushed and sieved to obtain 10–20 mesh granules for testing. The 1/16-inch extrudates were broken into pieces about 1/8-inch long. Each sample was calcined in an oven for four hours and stored in a dessicator until weighed and charged to the test reactor. The RE-Y catalyst was calcined at 600° F., while all other catalysts were calcined at 1000° F.

The catalyst screening tests were carried out in an upflow liquid-phase reactor as follows. The bottom portion of a 3/8-inch diameter tubular reactor was filled with quartz granules to act as preheat zone. Two to three grams of catalyst, depending on zeolite content, was charged on top of the quartz bed. Dry nitrogen was flowed over the catalyst at atmospheric pressure while the reactor was heated to 325° F. by a three-zone electric furnace. The temperature was measured by a sheathed thermocouple positioned just above the top of the catalyst bed. The control valve was then closed and the unit pressurized to 600 psig. The nitrogen was then turned off and benzene flow started at 12 ml/h. Pressure was maintained by diluting the reactor effluent with sufficient nitrogen to vaporize all the expected reaction products and passing the combined stream through the heated control valve. The vaporized product was analyzed by an on-stream gas chromatograph. After the GC analysis confirmed that the reactor was filled with liquid benzene, liquid propylene was injected into the benzene feed stream at a rate of 1.5 ml/h. The WHSV (grams of benzene+propylene fed per gram of catalyst per hour) was 5.7 for the pure zeolites and 4.6 for the extruded catalysts. The WHSV was lower for the extruded catalysts to compensate for the dilution effect of the binder.

Table 2 shows the propylene conversion and product composition on a benzene-free weight basis near the start and finish of each run. The product stream was analyzed every two hours and the results given herein are based on the average for the period shown.

TABLE 2

| Zeolite Beta | Zeolite Beta |

TABLE 2-continued

|  | Without Ammonium Exchange | | After One Ammonium Exchange | | Zeolite Beta 1/16-inch Extrudates | |
| --- | --- | --- | --- | --- | --- | --- |
| Hours on Stream | 13-17 | 143-165 | 9-19 | 631-653 | 9-21 | 479-501 |
| Propylene Conv. % | 100.0 | 100.0 | 100.0 | 100.0 | 100.0 | 100.0 |
| Product, Wt. % | | | | | | |
| Ethylbenzene | 0.0 | 0.0 | 0.0 | 0.0 | 0.0 | 0.0 |
| Cumene | 93.9 | 93.7 | 94.1 | 93.1 | 93.7 | 93.1 |
| N-propylbenzene | 0.0 | 0.0 | 0.0 | 0.0 | 0.0 | 0.0 |
| 1,3-DIPB | 3.7 | 3.9 | 3.8 | 4.2 | 3.9 | 4.1 |
| 1,4-DIPB | 2.2 | 2.3 | 1.9 | 2.6 | 2.1 | 2.7 |
| 1,3,5-TIPB | 0.0 | 0.0 | 0.0 | 0.0 | 0.0 | 0.0 |
| Other | 0.1 | 0.1 | 0.2 | 0.1 | 0.3 | 0.1 |

|  | Linde ELZ-6 Omega Zeolite | | Linde LZ-Y82 Steam Stabilized Y Zeolite Powder | | Linde LZ-Y82 Steam Stabilized Y Zeolite Extrudate | | |
| --- | --- | --- | --- | --- | --- | --- | --- |
| Hours on Stream | 9-21 | 191-213 | 9-15 | 71-93 | 7-21 | 95-117 | 623-645 |
| Propylene Conv. % | 100.0 | 89.9 | 100.0 | 100.0 | 100.0 | 100.0 | 100.0 |
| Product, Wt. % | | | | | | | |
| Ethylbenzene | 0.0 | 0.0 | 0.1 | 0.0 | 0.2 | 0.0 | 0.0 |
| Cumene | 88.1 | 87.1 | 95.4 | 87.6 | 92.1 | 84.0 | 81.6 |
| N-propylbenzene | 0.0 | 0.0 | 0.1 | 0.0 | 0.1 | 0.0 | 0.0 |
| 1,3-DIPB | 3.9 | 3.8 | 2.9 | 7.8 | 4.5 | 9.6 | 10.4 |
| 1,4-DIPB | 6.2 | 6.7 | 1.2 | 3.9 | 2.3 | 5.6 | 6.6 |
| 1,3,5-TIPB | 0.1 | 0.1 | 0.0 | 0.2 | 0.1 | 0.5 | 0.5 |
| Other | 1.7 | 2.3 | 0.3 | 0.4 | 0.7 | 0.8 | 0.8 |

|  | Linde SK-500 Rare Earth Y Zeolite | | ZSM-5 Zeolite |
| --- | --- | --- | --- |
| Hours on Stream | 7-21 | 321-333 | 9-23 |
| Propylene Conv. % | 100.0 | 99.8 | 97.4 |
| Product, Wt. % | | | |
| Ethylbenzene | 0.0 | 0.0 | — |
| Cumene | 81.5 | 76.9 | 90.4 |
| N-propylbenzene | 0.0 | 0.0 | 0.1 |
| 1,3-DIPB | 10.9 | 11.2 | 2.1 |
| 1,4-DIPB | 6.3 | 9.1 | 4.7 |
| 1,3,5-TIPB | 0.8 | 1.3 | 0.0 |
| Other | 0.5 | 1.6 | 2.6 |

The results in Table 2 show that zeolite beta made more of the desired monoalkylated product and less polyalkylated products than the prior art catalysts. Surprisingly, zeolite beta was the only catalyst able to make a product containing better than 90 wt.% cumene for more than 100 hours on stream.

Runs with zeolites ZSM-5, omega, and RE-Y were terminated after relatively short times on stream due to propylene breakthrough, whereas the zeolite beta catalysts were still giving 100% propylene conversion and a product containing better 90 wt.% cumene at end of run. Two of the beta zeolite runs exceeded 500 hours.

The steam stabilized Y zeolite catalysts were initially very selective for cumene production, but rapidly lost transalkylation activity. As a result, after only 100 hours on stream, cumene in the product had fallen below 88 wt.%.

In cumene production, product purity is an important consideration. The zeolite beta catalysts made less than 500 wt-ppm total n-propylbenzene and ethylbenzene based on cumene. After distillation, cumene made with the zeolite beta catalysts in this example would easily meet a 99.9 wt.% purity specification. On the other hand, ethylbenzene and n-propylbenzene in the products made with ZSM-5 and fresh steam stabilized Y zeolite exceeded 1000 wt-ppm based on cumene, making it much more difficult to meet the 99.9% purity specification.

Example 5

Staged Addition of Propylene in Cumene Synthesis

The synthesis of cumene in an adiabatic reactor with staged addition of propylene was approximated as follows. The reaction was carried out in five steps with equal amounts of propylene added in each of the first four steps. The product from each step was collected for further reaction in the next step at a higher temperature corresponding to the estimated adiabatic temperature rise. In the first step, benzene and propylene were passed over two grams of zeolite beta 10-20 mesh granules at rates of 48 ml/h and 1.5 ml/h, respectively. After an initial lineout period, the product was collected in a cold trap for two days and analyzed by gas chromatography. The product from the first reaction step was then reacted with additional propylene at the same feed rates as above, that is, 48 ml/h of product from the first reaction step and 1.5 ml/h of propylene. The second product was collected and the procedure was repeated for two additional steps. In the final reaction step the product from the fourth step was passed over the zeolite beta catalyst at a rate of 24 ml/h without propylene addition to simulate a transalkylation zone. The results are summarized in Table 3. The "% Propylene Added" and the Product Wt.% are cumulative numbers up to and including the step indicated.

TABLE 3

| | Step | | | | |
|---|---|---|---|---|---|
| | 1 | 2 | 3 | 4 | 5 |
| Temperature, °F. | 262.5 | 287.5 | 312.5 | 337.5 | 350.0 |
| % Propylene Added | 25% | 50% | 75% | 100% | 100% |
| Product Wt. % | | | | | |
| Cumene | 97.13 | 96.35 | 95.13 | 94.23 | 95.48 |
| N-Propylbenzene | 0.004 | 0.008 | 0.014 | 0.023 | 0.028 |
| 1,3-DIPB | 1.32 | 1.78 | 2.58 | 3.32 | 2.71 |
| 1,4-DIPB | 0.87 | 1.48 | 1.93 | 2.04 | 1.36 |
| 1,3,5-TIPB | 0.00 | 0.00 | 0.00 | 0.00 | 0.00 |
| Other | 0.68 | 0.48 | 0.34 | 0.37 | 0.41 |

This experiment demonstrates that cumene can be produced with high selectivity in a zeolite beta catalyzed process where there is stepwise addition of propylene. A further advantage of adding propylene in this fashion is that the ratio of benzene to olefin is always very high which reduces the rate of catalyst fouling.

Example 6

Production of Ethylbenzene by the Alkylation of Benzene with Ethylene

Zeolite beta was prepared by the same method described in Example 1. The zeolite was ammonium exchanged once to remove sodium, mixed with peptized alumina, and formed into 1/16" extrudates. The extrudates were calcined at 400° F.–1000° F. On a dry basis, the final catalyst was 80% zeolite beta and 20% alumina.

The catalyst was tested for ethylbenzene synthesis using the same procedure and apparatus described for cumene catalyst screening in Example 4, except that the reaction pressure was 450 psig and ethylene, instead of propylene, was injected into the benzene stream as a gas to give a 7.0/1.0 benzene-to-ethylene feed molar ratio. The temperature was 325° F. and WHSV was 4.6. Under these conditions, ethylene conversion was 100% and the product comprised 91.1% ethylbenzene, 7.9% diethylbenzenes, 0.3% triethylbenzenes and 0.7% other products, on a benzene-free weight basis.

In a comparative run, when a steam stabilized Y zeolite catalyst (Linde LZ-Y82) was tested under the same conditions as above, the product comprised 82% ethylbenzene, 8.4% diethylbenzenes, 0.7% triethylbenzenes and 8.8% other products, on a benzene free weight basis.

Example 7

Comparison of Zeolite Catalysts in a Transalkylation Process for the Production of Cumene Cumene bottoms containing di- and triisopropylbenzene from a zeolite-catalyzed alkylation process were blended with benzene in one-to-four weight ratio to obtain a transalkylation feedstock. Table 4 compares results obtained when this feedstock was reacted over steam stabilized Y (Linde LZ-Y82), omega (Linde ELZ-6), rare earth Y (Linde SK-500), and zeolite beta catalysts. The composition of the feedstock is also provided in Table 4.

Each of the catalysts was obtained as 1/16 extrudates. The zeolite beta catalyst was prepared from 80% zeolite beta (Si/Al=13) and 20% alumina binder. The sodium content of the extrudates was less than 200 ppm. The extrudates were broken into pieces about 1/8" long, calcined, and charged to a reactor as described in Example 4. The reaction was conducted at 4.3 WHSV, 325° F., and 600 psig.

The ratios of cumene to diisopropylbenzene in Table 4 show that the zeolite beta and steam stabilized Y zeolite were much more active transalkylation catalysts than the omega or rare earth Y zeolites. Zeolite beta is preferred to steam stabilized Y for this purpose because it makes a product which contains less ethylbenzene and n-propylbenzene and deactivates more slowly. The slower rate of deactivation is shown in Example 8.

TABLE 4

| | Feed | Product Using Steam Stabilized Y Zeolite | Product Using Omega Zeolite |
|---|---|---|---|
| Hours on Stream | | 6–24 | 6–24 |
| Composition, Wt % | | | |
| benzene | 80.0 | 72.9 | 77.2 |
| ethylbenzene | 0.00 | 0.15 | 0.00 |
| cumene | 0.5 | 24.5 | 2.3 |
| n-propylbenzene | 0.00 | 0.04 | 0.00 |
| 1,3-DIPB | 10.7 | 1.5 | 11.9 |
| 1,4-DIPB | 7.4 | 0.6 | 7.4 |
| 1,3,5-TIPB | 0.3 | 0.04 | 0.4 |
| Other | 1.0 | 0.3 | 0.8 |
| cumene/DIPB | 0.03 | 11.7 | 0.12 |

| | Product Using Rare Earth Exchanged Y Zeolite | Product Using Zeolite Beta |
|---|---|---|
| Hours on Stream | 6–24 | 6–24 |
| Composition, Wt % | | |
| benzene | 75.7 | 73.1 |
| ethylbenzene | 0.00 | 0.00 |
| cumene | 6.1 | 19.2 |
| n-propylbenzene | 0.00 | 0.00 |
| 1,3-DIPB | 10.9 | 4.3 |
| 1,4-DIPB | 6.3 | 2.1 |
| 1,3,5-TIPB | 0.4 | 0.4 |
| Other | 0.6 | 0.9 |
| cumene/DIPB | 0.35 | 3.0 |

Example 8

Comparison of Deactivation Rate of Zeolite Beta and Steam Stabilized Y Zeolite in Transalkylation of Diisopropylbenzene With Benzene The deactivation rate of zeolite beta and steam stabilized Y zeolite (Linde LZ-Y82) when transalkylating diisopropylbenzene (DIPB) to cumene were compared by carrying out two experiments. Cumene column bottoms (CCB) from a zeolite-based alkylation process were blended with benzene (BZ) in a weight ratio of 2/1 BZ/CCB. The CCB contained 90–95 wt.% DIPB with the remainder being higher boiling components. For each run, the catalyst was first crushed and then sieved using U.S.A. Standard Testing Sieves (A.S.T.M. E-11 Specification). Particles in the 12–28" mesh range were collected and charged to a ½-inch diameter reactor. The zeolite beta catalyst was prepared from 65% zeolite beta and 35% alumina binder. Each experiment was carried out at a liquid hourly space velocity (LHSV) of 1 and a reactor pressure of 500 psig. During each experiment the reactor temperature was controlled to convert 35–40% of the DIPB. The initial reactor temperature was 280° F. for each experiment. After 57 days on stream the deactivation rate of the steam stabilized Y zeolite catalyst was 0.8° F./day. The deactivation rate of the zeolite beta was 0.4° F./day after 68 days on stream. Reactor temperatures at three points in time with each catalyst are shown in Table 5 below.

TABLE 5

| | Time on stream, days | | |
|---|---|---|---|
| | 20 | 30 | 54 |
| Reactor temperature, °F. | | | |
| Steam Stabilized Y zeolite | 348 | 352 | 375 |
| Zeolite beta | 308 | 310 | 320 |
| Change In Temperature Over this 34-Day Period, °F. (Day 20 to Day 54) | | | |
| Steam Stabilized Y Zeolite | | | 27 |
| Zeolite Beta | | | 12 |
| Deactivation Rate Over This 34-day Period, °F./Day | | | |
| Steam Stabilized Y Zeolite | | | 0.8 |
| Zeolite Beta | | | 0.35 |

What is claimed is:

1. A process for the alkylation of an aromatic hydrocarbon which comprises contacting a stoichiometric excess of the aromatic hydrocarbon with a $C_2$ to $C_4$ olefin under at least partial liquid phase conditions and in the presence of a catalyst comprising zeolite beta wherein there are at least two catalyst beds or reactors in series and at least a portion of the aromatic hydrocarbon is added between the catalyst beds or reactors.

2. The process according to claim 1, wherein the molar ratio of aromatic hydrocarbon to olefin is at least about 4:1.

3. The process according to claim 1, wherein the aromatic hydrocarbon is a member selected from the group consisting of benzene, toluene and xylene, or mixtures thereof.

4. The process according to claim 3, wherein the aromatic hydrocarbon is benzene.

5. The process according to claim 1, wherein the olefin is a member selected from the group consisting of ethylene, propylene, butene-1, trans-butene-2 and cis-butene-2, or mixtures thereof.

6. The process according to claim 5, wherein the olefin is propylene.

7. The process according to claim 5, wherein the olefin is ethylene.

8. The process according to claim 1, wherein the alkylation reaction is carried out at a temperature in the range of about 250° F. to 450° F. and a pressure in the range of about 50 psig to 1000 psig.

9. The process according to claim 1, wherein the alkylation reaction is carried out at a weight hourly space velocity of about 0.5 to 50.

10. The process according to claim 1, wherein a major portion of the cation sites in the zeolite beta are occupied by hydrogen ions and/or rare earth ions.

11. The process according to claim 1, wherein the zeolite beta has a silicon to aluminum atomic ratio greater than 5:1 and less than 100:1.

12. The process according to claim 11, wherein the zeolite beta has a silicon to aluminum atomic ratio greater than 5:1 and less than about 50:1.

13. The process according to claim 1, wherein the zeolite beta is combined with an inorganic oxide binder in an amount ranging from about 1 to 99 weight percent of zeolite beta 14. The process according to claim 13, wherein the inorganic oxide binder is alumina.

15. The process according to claim 1, wherein the aromatic hydrocarbon is benzene and the olefin is propylene.

16. The process according to claim 1, wherein the aromatic hydrocarbon is benzene and the olefin is ethylene.

* * * * *